United States Patent
D'Antonio

(10) Patent No.: US 10,336,777 B2
(45) Date of Patent: Jul. 2, 2019

(54) CYSTEINE-MODIFYING SUBSTRATE ANALOGUE INHIBITORS OF RIBOSE 5-PHOSPHATE ISOMERASE FOR PARASITIC DISEASES, ALONG WITH METHODS OF THEIR FORMATION AND USE

(71) Applicant: University of South Carolina, Columbia, SC (US)

(72) Inventor: Edward L. D'Antonio, Bluffton, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/888,158

(22) Filed: Feb. 5, 2018

(65) Prior Publication Data

US 2018/0155373 A1    Jun. 7, 2018

Related U.S. Application Data

(62) Division of application No. 15/360,139, filed on Nov. 23, 2016, now Pat. No. 10,065,978.

(60) Provisional application No. 62/259,172, filed on Nov. 24, 2015.

(51) Int. Cl.
*C07F 9/09* (2006.01)
*C07F 9/655* (2006.01)
*C07F 9/6574* (2006.01)
*C07F 9/24* (2006.01)

(52) U.S. Cl.
CPC ............ *C07F 9/091* (2013.01); *C07F 9/2408* (2013.01); *C07F 9/65515* (2013.01); *C07F 9/65744* (2013.01)

(58) Field of Classification Search
CPC ...................................................... C07F 9/091
See application file for complete search history.

(56) References Cited

U.S. PATENT DOCUMENTS

| 4,761,404 A | 8/1988 | Bugianesi et al. |
| 6,551,600 B2 | 4/2003 | Hawkins et al. |
| 8,618,080 B2 | 12/2013 | Bauer et al. |

OTHER PUBLICATIONS

Gibson et al (1980):STN International, HCAPLUS database (Columbus, Ohio), Accession No. 1980: 563504.*
Plaksina et al (1982):STN International, HCAPLUS database (Columbus, Ohio), Accession No. 1982: 176916.*
Stern, A.L., Naworyta, A., Cazzulo, J.J., and Mowbray, S.L. (2011) Structures of type B ribose 5-phosphate isomerase from Trypanosoma cruzi shed light on the determinants of sugar specificity in the structural family. 278, 793-808.
Stern, A.L., Burgos, E., Salmon, L., and Cazzulo, J.J. (2007) Ribose 5-phosphate isomerase type B from Trypanosoma cruzi: kinetic properties and site-directed mutagenesis reveal information about the reaction mechanism. 401, 279-285.
Ruda et al. (2007) Synthesis and biological evaluation of phosphate prodrugs of 4-phospho-D-erythronohydroxamic acid, an inhibitor of 6-phosphogluconate dehydrogenase.
Ruda et al. (2010) Aryl phosphoramidates of 5-phospho erythronohydroxamic acid, a new class of potent trypanocidal compounds. J. Med. Chem. 53, 6071-6078.
Lefebvre et al. (1995) Mononucleoside phosphotriester derivatives with S-acyl-2-thioethyl bioreversible phosphate-protecting groups: Intracellular delivery of 3'-azido-2',3'-dideoxythymidine 5'-monophosphate. J. Med. Chem. 38, 3941-3950.

* cited by examiner

*Primary Examiner* — Golam M Shameem
(74) *Attorney, Agent, or Firm* — Dority & Manning, PA

(57) ABSTRACT

Compounds are generally provided, along with pharmaceutical compositions including such compounds. Methods are also generally provided for inhibiting ribose 5-phosphate isomerase in a human, such as via administering to the human the pharmaceutical composition that includes such a compound. Methods are also generally provided for treating a mammal that is infected by a parasitic organism, such as via administering to the mammal the pharmaceutical composition that includes such a compound. Methods are also generally provided for forming a pharmaceutical composition.

10 Claims, 9 Drawing Sheets

CYSTEINE-MODIFYING SUBSTRATE ANALOGUE INHIBITORS OF RIBOSE 5-PHOSPHATE ISOMERASE FOR PARASITIC DISEASES, ALONG WITH METHODS OF THEIR FORMATION AND USE

CROSS REFERENCE TO RELATED APPLICATIONS

The present application is a divisional application of and claims priority to U.S. patent application Ser. No. 15/360,139, having a filing date of Nov. 23, 2016, which claims filing benefit of U.S. Provisional Patent Application Ser. No. 62/259,172 titled "Cysteine-Modifying Substrate Analogue Inhibitors of Ribose 5-Phosphate Isomerase for Parasitic Diseases, Along with Methods of Their Formation and Use" of D'Antonio filed on Nov. 24, 2015, the disclosure of which is incorporated by reference herein.

BACKGROUND

Kinetoplastid parasites, such as *Trypanosoma cruzi* (*T. cruzi*), *Trypanosoma brucei* (*T. brucei*), and *Leishmania* spp., utilize and depend on the pentose phosphate pathway (PPP) for the reducing agent NADPH and also rely on the PPP for support for nucleic acid and nucleotide biosynthesis. The PPP is essential for these organisms and obstruction of the pathway leads to cell death and can be caused by inhibition (using a drug) of the enzyme, ribose 5-phosphate isomerase. In order to create a therapeutic drug, an inhibitor would need to selectively block the parasite homologue and avoid cross-reactivity with the human homologue (bind weaker or not bind at all), giving rise to a good selectively ratio.

*T. cruzi* is the causative agent for Chagas' disease and benznidazole and nifurtimox are the two main clinically-available treatments available in Latin America. These drugs have the potential for resistance because they were developed over 35 years ago and alternative drugs have not emerged. *T. brucei* is the causative agent for human African sleeping sickness and various drugs are available, such as pentamidine, suramin, eflornithine, and melarsoprol. *Leishmania* spp. are protozoan parasites causing Leishmaniasis and medical intervention requires treatment such as pentavalent antimony-based medicines, or more expensive treatments such as amphotericin B, miltefosine, or paramomycin. The drugs for these kinetoplasid diseases all require substantial improvements in their tolerability, safety, and efficacy.

A need exists for new drugs that strongly bind to drug targets found in these parasites. Such a need includes inhibitors of the enzyme ribose 5-phosphate isomerase (RPI).

SUMMARY

Objects and advantages of the invention will be set forth in part in the following description, or may be obvious from the description, or may be learned through practice of the invention.

Compounds are generally provided, along with pharmaceutical compositions including such compounds. In one embodiment, a compound is generally provided that has the formula:

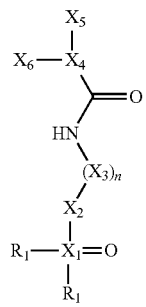

where: $R_1$ is, independently, H, OH, $NH_2$, SH, O, a halogen, or an organic phosphate masking group; $X_1$ is P, O, N, B, or S; $X_2$ is $CH_2$, O, NH, or SH; $X_3$ is an organic linkage; n is an integer from 0 to 5; $X_4$ is CH, $CH_2$, SH, O, NH, or S; $X_5$ is H, CH, $CH_2$, $CH_3$, NH, SH, S, B, O, or a halogen; and $X_6$ is H, CH, $CH_2$, $CH_3$, NH, SH, S, B, O, or a halogen.

Methods are also generally provided for inhibiting ribose 5-phosphate isomerase in a human, such as via administering to the human the pharmaceutical composition that includes such a compound.

Methods are also generally provided for treating a mammal that is infected by a parasitic organism, such as via administering to the mammal the pharmaceutical composition that includes such a compound.

Methods are also generally provided for forming a pharmaceutical composition, which may include mixing a solution of diisopropylphosphoramidous dichloride and 2-(S-pivaloylthio)ethanol to form a first compound; mixing a solution of the first compound and N-(tert-butoxycarbonyl) ethanolamine to produce a first mixture; subjecting the first mixture to oxidation and allowing a reaction to proceed to produce a second compound; mixing a solution containing the second compound and anhydrous HCl (4 N) in dioxane to form a third compound; and mixing a solution of the third compound with iodoacetic acid N-hydroxy-succinimide ester to produce the compound.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1A:
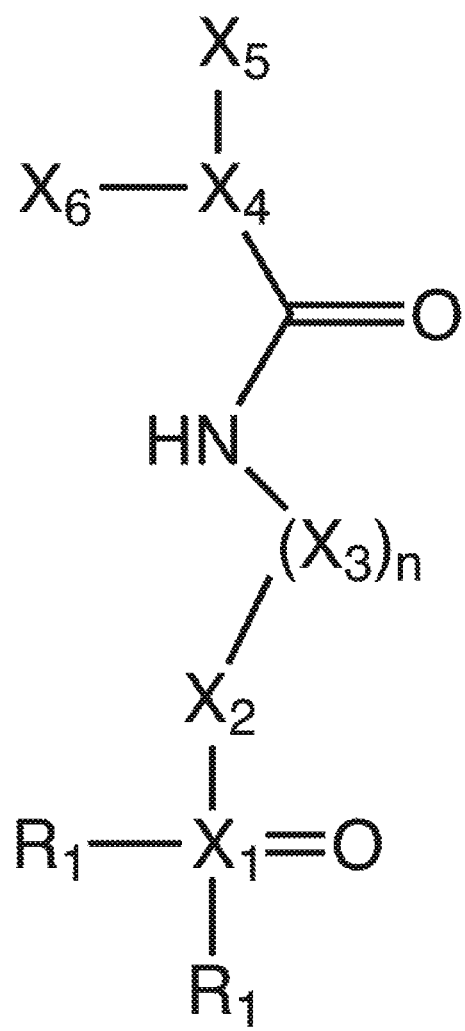
FIG. 1A shows an exemplary composition that is a ribose 5-phosphate isomerase type B inhibitor.

Repeat use of reference characters in the present specification and drawings is intended to represent the same or analogous features or elements of the present invention.

DEFINITIONS

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

As used herein, the term "related compounds thereof" refers to compounds that have the basic structure of the base compound with substituted atom(s) and/or substituted side groups, while still keeping the functionality of the base compound.

The term "pharmaceutically effective amount" refers to the amount of a drug or pharmaceutical agent that will elicit the biological or medical response of a tissue, system, animal, or human that is being sought by a researcher or clinician. This amount can be a therapeutically effective amount.

The term "pharmaceutically acceptable carrier" is used herein to refer to a carrier that is useful in preparing a pharmaceutical composition that is generally safe, non-toxic and neither biologically nor otherwise-undesirable, and is acceptable for veterinary use as well as human pharmaceutical use. A "pharmaceutically acceptable carrier" as used in the specification and claims can include both one and more than one such carrier. By "pharmaceutically acceptable" it is meant the carrier must be compatible with the other ingredients of the formulation and not deleterious to the recipient thereof.

The terms "administration of" or "administering a" pharmaceutical composition should be understood to mean providing a pharmaceutical composition to an individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The term "treatment" or "treating" means any administration of a pharmaceutical composition to obtain a desired pharmacologic and/or physiologic effect. The effect may be prophylactic in terms of completely or partially preventing a disease or symptom thereof, and/or may be therapeutic in terms of a partial or complete cure for a disease and/or adverse effect attributable to the disease. Treatment includes (a) inhibiting the disease in the subject that is experiencing or displaying the pathology or symptomatology of the diseased (i.e., arresting further development of the pathology and/or symptomatology), or (b) ameliorating the disease in the subject that is experiencing or displaying the pathology or symptomatology of the diseased (i.e., reversing the pathology and/or symptomatology).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Compounds and methods are generally provided that can be used against certain drug-targets (e.g., ribose 5-phosphate isomerase) that are found in protozoan parasites. The drugs proposed in this patent may serve as viable substitutes for the currently used drugs in the clinic, pending in vitro parasite studies and mouse infectivity studies. The compounds described herein are experimentally-confirmed potent & selective inhibitors of *T. cruzi* ribose 5-phosphate isomerase type B. Human ribose 5-phosphate isomerase exists only as a type A and does not include the reactive cysteine (Cys-69) found in *T. cruzi*. The drug compounds described in this patent application may offer an alternative to the mainstream drugs that are used in the clinic for three diseases of the trypanosome, such as American Trypanosomiasis (Chagas' Disease), Human African Trypanosomiasis (Human African Sleeping Sickness), and Leishmaniasis caused by parasites *T. cruzi, T. brucei*, and *Leishmania* spp., respectively.

I. Ribose 5-Phosphate Isomerase Inhibitor Compounds

Figure 5A:
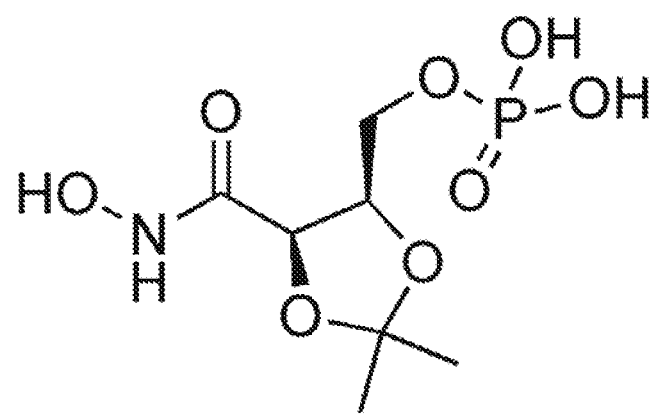
FIG. 5A shows an exemplary compound having a phosphate group.
Figure 5B:
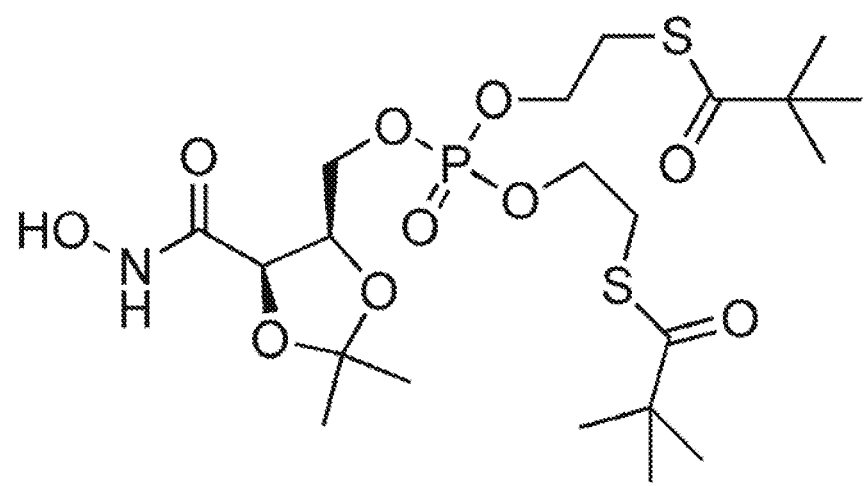
FIG. 5B shows an exemplary compound having a phosphate group and an organic masking group attached to the phosphate group.
Figure 5C:
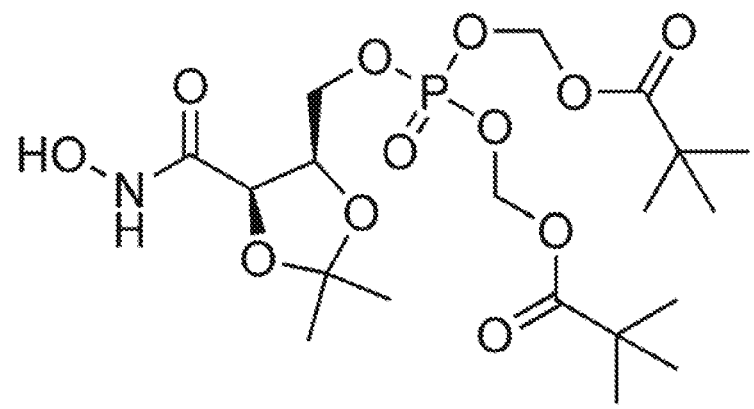
FIG. 5C shows another exemplary compound having a phosphate group and an organic masking group attached to the phosphate group.
Figure 5D:
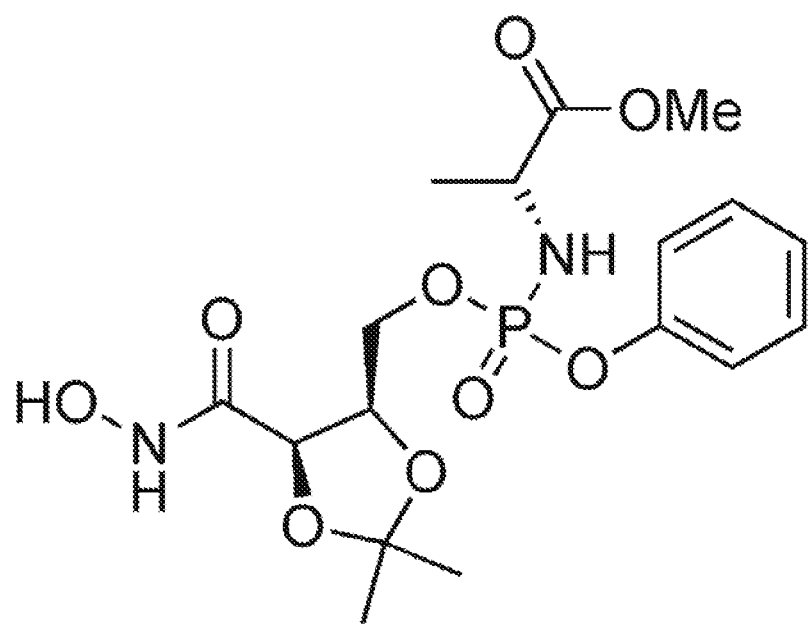
FIG. 5D shows yet another exemplary compound having a phosphate group and an organic masking group attached to the phosphate group.
Figure 5E:
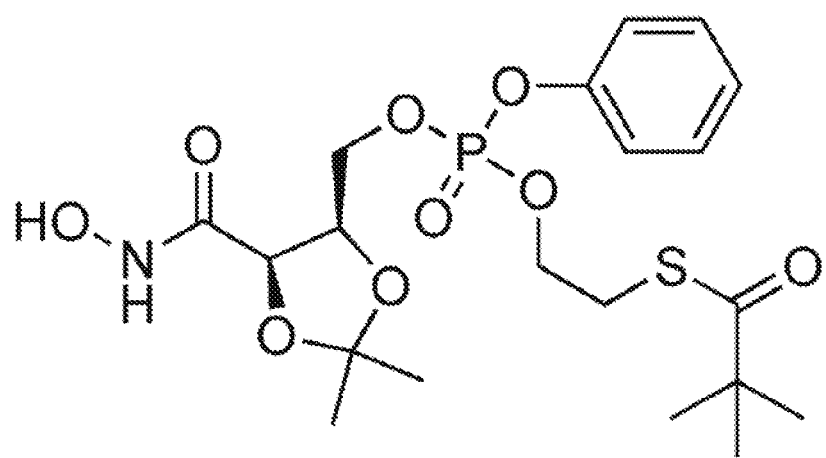
FIG. 5E shows still another exemplary compound having a phosphate group and an organic masking group attached to the phosphate group.
Figure 5F:
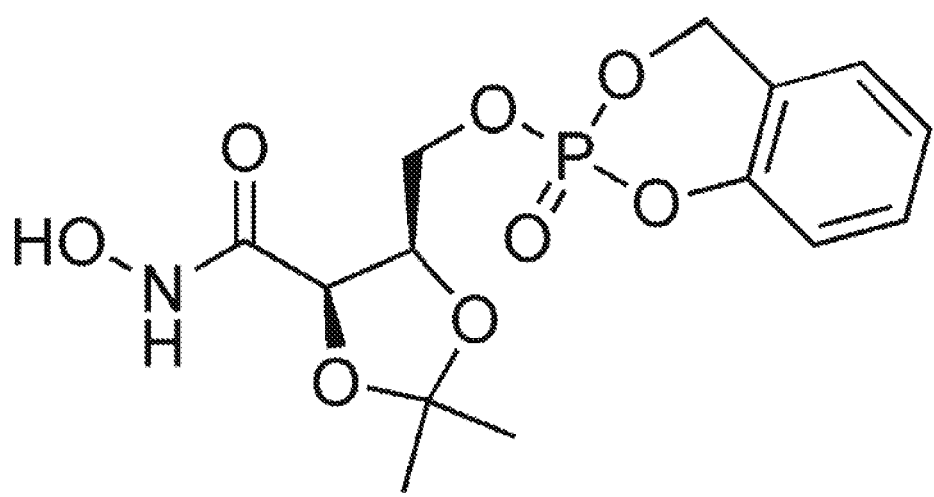
FIG. 5F shows still another exemplary compound having a phosphate group and an organic masking group attached to the phosphate group.

In one embodiment, FIG. 1A shows an exemplary composition, including a ribose 5-phosphate isomerase type B inhibitor, where:

$R_1$ is, independently, H, OH, $NH_2$, SH, O, a halogen (e.g., F, Cl, Br, or I), or an organic phosphate masking group (or another organic masking group);

$X_1$ is P, O, N, B, or S;

$X_2$ is $CH_2$, O, NH, or SH;

$X_3$ is an organic linkage, such as $CH_2$;

n is an integer from 0 to 5 (e.g., 0, 1, 2, 3, 4, or 5);

$X_4$ is CH, $CH_2$, SH, O, NH, or S;

$X_5$ is H, CH, $CH_2$, $CH_3$, NH, SH, S, B, O, or a halogen (e.g., F, Cl, Br, or I); and $X_6$ is H, CH, $CH_2$, $CH_3$, NH, SH, S, B, O, or a halogen (e.g., F, Cl, Br, or I). In particular embodiments, the organic masking group can be any of the moiety groups, which are masking the phosphate of FIG. 5A, shown in FIGS. 5B-5F (e.g., FIG. 5B reveals two [tert-butyl]-S-acyl-2-thioethyl substituents masking the phosphate group of the compound).

Figure 1B:
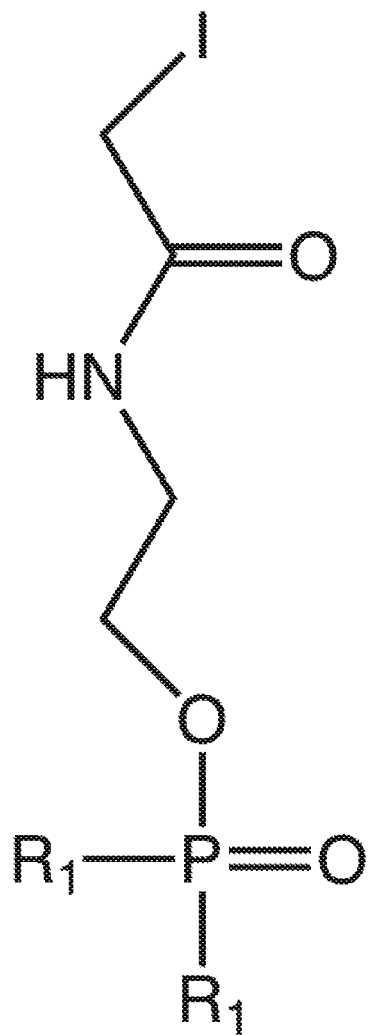
FIG. 1B shows an embodiment of the exemplary composition FIG. 1A where $X_1$ is P, $X_2$ is O, $X_3$ is $CH_2$, n is 2, $X_4$ is CH, $X_5$ is I, and $X_6$ is H.

In particular embodiments of the composition, each $R_1$ is, independently, an organic phosphate masking group; $X_1$ is P; $X_2$ is O, $X_3$ is $CH_2$; n is 0, 1, 2, 3, 4, or 5 (e.g., n is 2); $X_4$ is CH; $X_5$ is I; and $X_6$ is H. For example, FIG. 1B shows an embodiment where each $R_1$ is, independently, an organic phosphate masking group; $X_1$ is P; $X_2$ is O, $X_3$ is $CH_2$; n is 2; $X_4$ is CH; $X_5$ is I; and $X_6$ is H.

Figure 1C:
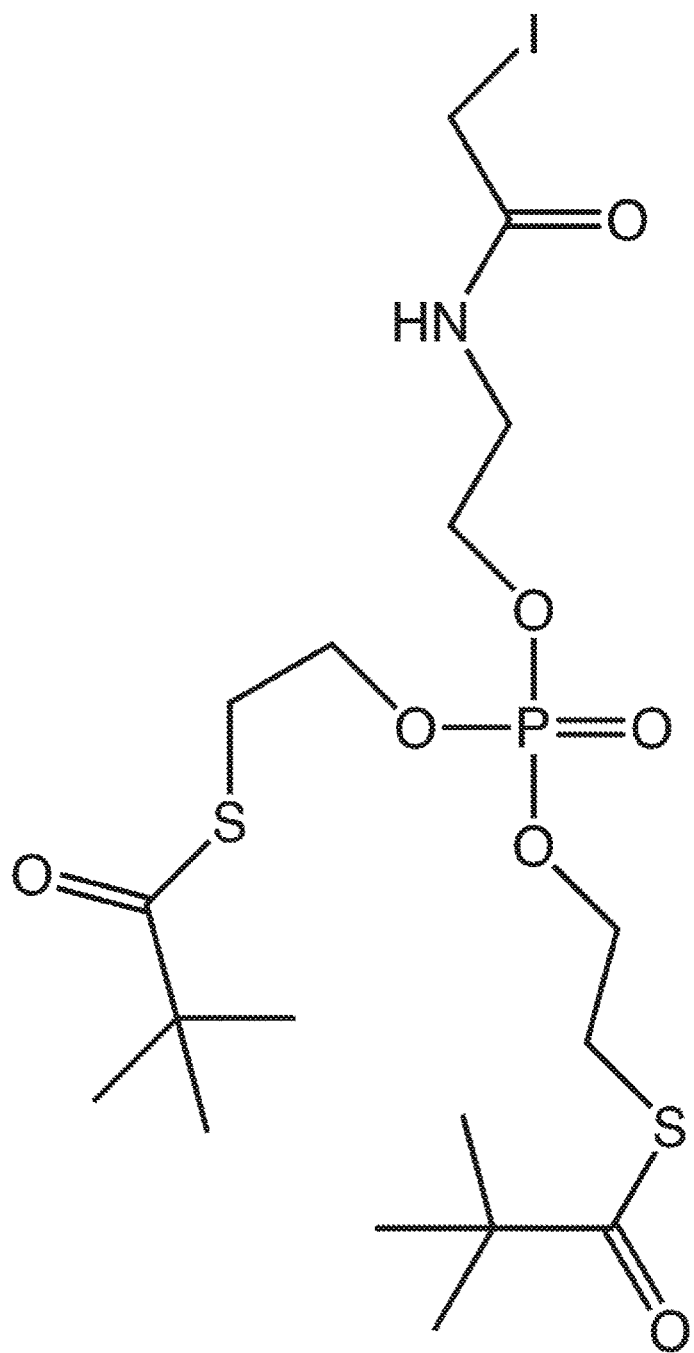
FIG. 1C shows an embodiment of the compound of FIG. 1B with phosphate masking groups formed from an acyl 2-thioethyl derivative having a pivalic terminal group (i.e., N-(2-{[bis({2-[(2,2-dimethylpropanoyl)sulfanyl]ethoxy}) phosphoryl]oxy}ethyl)-2-iodoacetamide)

The phosphate masking groups are configured to increase the activity of the inhibitors against *T. cruzi*, *T. brucei*, and *Leishmania* spp. by enhancing uptake of the drug through passive permeation across plasma membranes. FIG. 1C shows the compound of FIG. 1B with phosphate masking groups that are formed from an acyl 2-thioethyl derivative having a pivalic terminal group. In the particular embodiment of FIG. 1C, the inhibitor is the N-(2-{[bis({2-[(2,2-dimethylpropanoyl)sulfanyl]ethoxy})phosphoryl]oxy}ethyl)-2-iodoacetamide.

II. Pharmaceutical Compositions

In one embodiment, a pharmaceutical composition is generally provided that includes a pharmaceutically acceptable carrier and a ribose 5-phosphate isomerase inhibitor having the structure as shown in FIG. 1A, discussed above.

Pharmaceutical compositions may be prepared by any of the methods well known in the art of pharmacy. Pharmaceutical compositions encompass any compositions made by admixing the active ingredients and a pharmaceutically acceptable carrier. The carrier may take a wide variety of forms depending on the form of preparation desired for administration, e.g., oral or parenteral (including intravenous). Thus, the pharmaceutical composition can be presented as discrete units suitable for oral administration such as capsules, cachets, or tablets each containing a predetermined amount of the active ingredients. Further, the composition can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the composition may also be administered by controlled release means and/or delivery devices. The foregoing list is illustrative only and is not intended to be limiting in any way.

Pharmaceutical compositions intended for oral use may contain one or more agents selected from the group consisting of sweetening agents, flavoring agents, coloring agents and preserving agents in order to provide pharmaceutically elegant and palatable preparations. Tablets may contain a composition of FIG. 1A in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. A tablet may be prepared by compression or molding, optionally with one or more accessory ingredients or adjuvants. Compressed tablets may be prepared by compressing, in a suitable machine, a compound of FIG. 1A in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

Pharmaceutical compositions for oral use may also be presented as hard gelatin capsules wherein the compound of FIG. 1A is mixed with an inert solid diluent, for example, calcium carbonate, calcium phosphate or kaolin, or as soft gelatin capsules wherein the compound of FIG. 1A is mixed with water or an oil medium, for example peanut oil, liquid paraffin, or olive oil.

Pharmaceutical compositions can also include aqueous suspensions, which contain the active materials in admixture with excipients suitable for the manufacture of aqueous suspensions. In addition, oily suspensions may be formulated by suspending the compound of FIG. 1A in a vegetable oil, for example arachis oil, olive oil, sesame oil or coconut oil, or in a mineral oil such as liquid paraffin. Oily suspensions may also contain various excipients. The pharmaceutical compositions of FIG. 1A may also be in the form of oil-in-water emulsions, which may also contain excipients such as sweetening and flavoring agents.

Pharmaceutical compositions can be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of FIG. 1A, to produce a cream or ointment having a desired consistency.

Pharmaceutical compositions can also be in a form suitable for rectal administration wherein the carrier is a solid. Suitable carriers include cocoa butter and other materials commonly used in the art.

III. Methods of Inhibiting Ribose 5-Phosphate Isomerase

Methods are also provided for inhibiting ribose 5-phosphate isomerase, both in vitro and in vivo. In one embodiment, the method comprises contacting the ribose 5-phosphate isomerase with a compound having the structure of FIG. 1A, discussed above.

For instance, a method is provided for inhibiting ribose 5-phosphate isomerase in a parasitic organism. This method comprises administering to the human a composition comprising a pharmaceutically acceptable carrier and a ribose 5-phosphate isomerase inhibitor having the structure shown in FIG. 1A, described above. The parasitic organism can be of a disease associated by the parasite that contains ribose 5-phosphate isomerase, such as American Trypanosomiasis (Chagas' Disease), Human African Trypanosomiasis (African Sleeping Sickness), Leishmaniasis, Malaria, Schistosomaisis (Snail Fever), Filarial diseases, etc.

IV. Methods of Treatment

Also, a method is provided for treating a mammal that is infected by a parasitic organism. This method comprises administering to the disease-affected mammal a composition comprising a pharmaceutically acceptable carrier and the compound of FIG. 1A, described above. Examples of such disease-affected mammals include humans and domestic animals (e.g. dogs, cats, and thereof).

V. Methods of Formation

Figure 2:
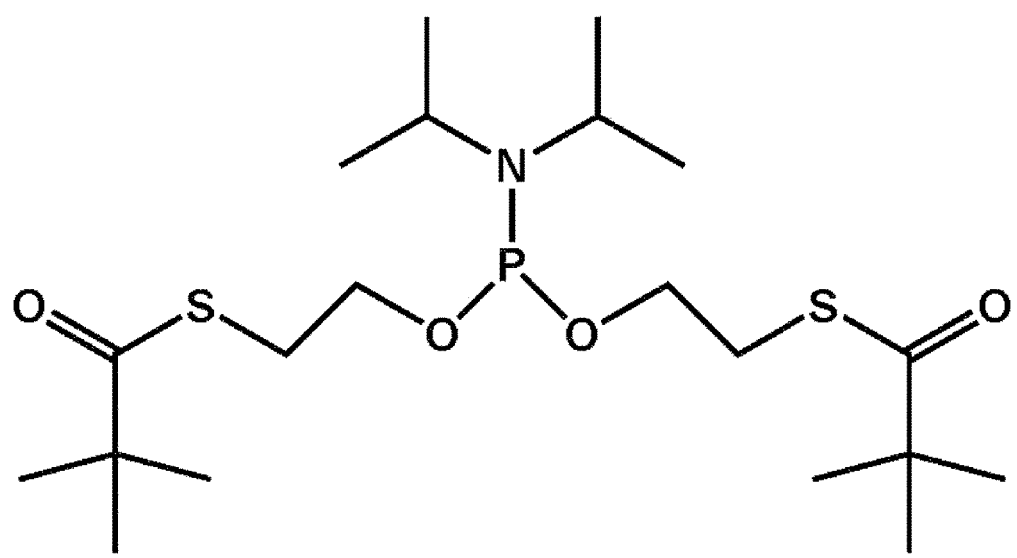
FIG. 2 shows an exemplary first compound that can be used in methods of forming the compounds of FIG. 1A.
Figure 3:
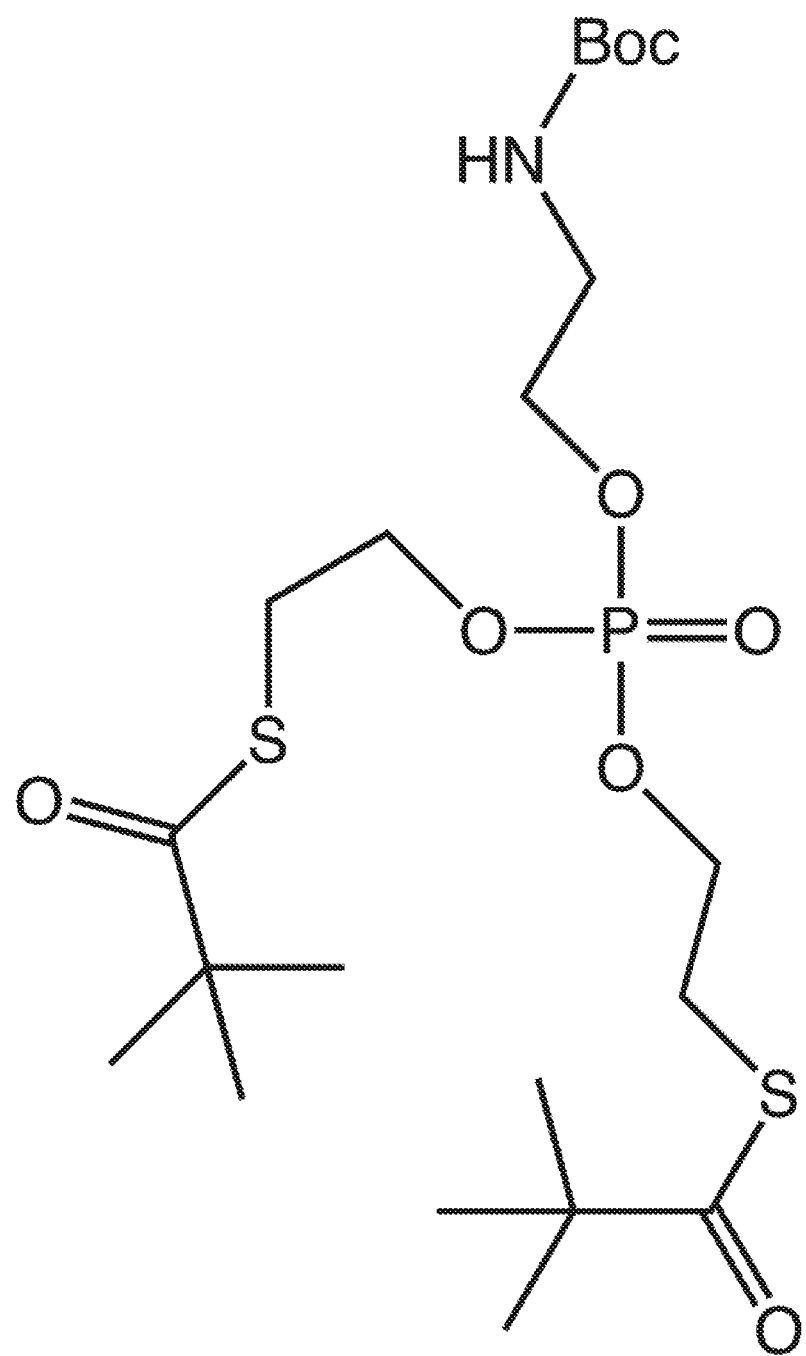
FIG. 3 shows an intermediate compound that can be formed and used in methods of forming the compounds of FIG. 1A.
Figure 4:
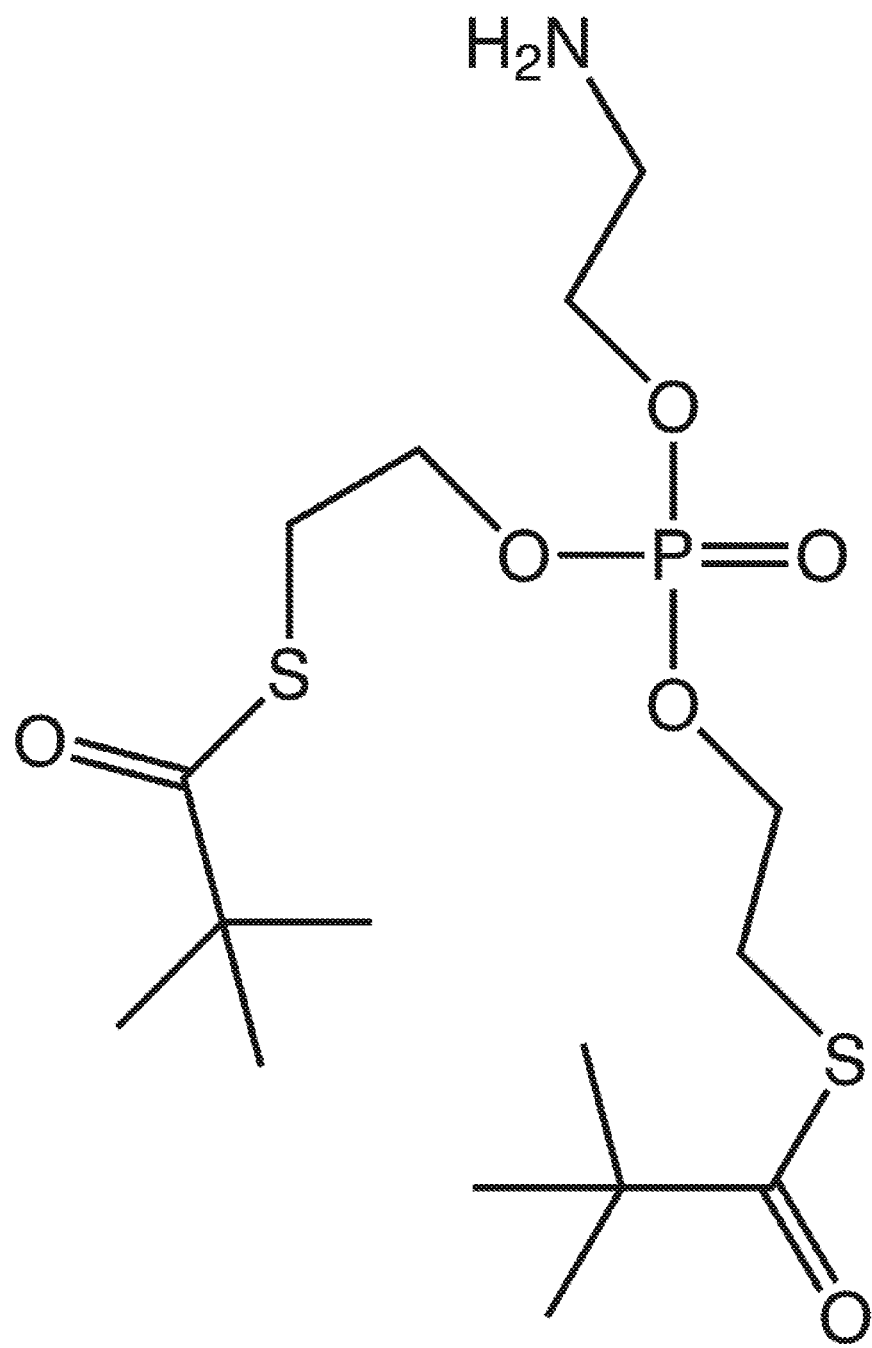
FIG. 4 shows an intermediate compound that can be formed and used in methods of forming the compounds of FIG. 1A.

Finally, a method is provided for forming the compound with the structure shown in FIG. 1C. In one embodiment, the method includes (a) mixing a solution of diisopropylphosphoramidous dichloride (1 equiv.) and 2-(S-pivaloylthio)ethanol (2 equiv.) in tetrahydrofuran with triethylamine (e.g., for 2 hours at −78° C. in an acetone/dry-ice bath) followed by purification by flash column chromatography to form a first compound, wherein the first compound is, with molecular formula $C_{20}H_{40}NO_4PS_2$, 8-[bis(propan-2-yl)amino]-2,2,14,14-tetramethyl-7,9-dioxa-4,12-dithia-8-phosphapentadecane-3,13-dione (see FIG. 2);

(b) mixing a solution containing the first compound and N-(tert-butoxycarbonyl)ethanolamine in tetrahydrofuran with tetraazacyclopentadiene (1-H-tetrazole) (e.g., for 2 hours at room temperature) to produce a first mixture (at which point the first mixture can be cooled to −78° C. using an acetone/dry-ice bath;

(c) subjecting the first mixture to oxidation by tert-butyl hydroperoxide and allowing the reaction to proceed (e.g., for 45 minutes with the reaction temperature being first held at −78° C. for the first 15 minutes followed by a gradual temperature gradient to room temperature) to produce a second compound (which can be purified by silica gel chromatography), wherein the second compound is, with molecular formula $C_{21}H_{40}NO_8PS_2$, tert-butyl N-(2-{[bis({2-[(2,2-dimethylpropanoyl)sulfanyl]ethoxy})phosphoryl]oxy}ethyl)carbamate (see FIG. 3);

(d) mixing the second compound with anhydrous HCl (4 N) in dioxane (e.g., at room temperature for 2 hr) for deprotection of the Boc group to produce a third compound, wherein the third compound is, with molecular formula $C_{16}H_{32}NO_6PS_2$, 1-[(2-{[(2-aminoethoxy)({2-[(2,2-dimethylpropanoyl)sulfanyl]ethoxy})phosphoryl]oxy}ethyl)sulfanyl]-2,2-dimethylpropan-1-one (see FIG. 4); and (e) mixing a solution of the third compound and the iodoacetic acid N-hydroxy-succinimide ester in tetrahydrofuran with triethylamine (pH should be observed in the range between 7.0-8.5) (e.g., at room temperature for 2 hr) to produce the compound (see FIG. 1C).

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

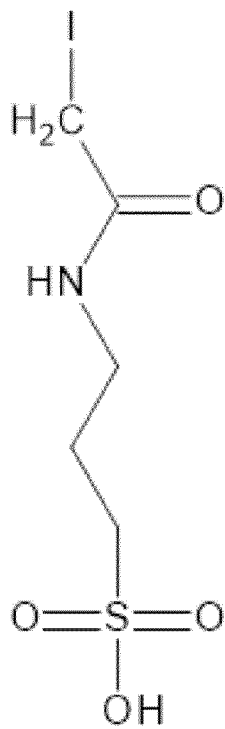

What is claimed:

1. A compound having the formula:

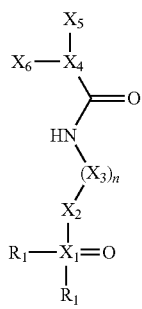

where:
$X_1$ is P and both $R_1$ are OH or $X_1$ is S, one $R_1$ is OH and the other $R_1$ is O;
$X_3$ is $CH_2$;
n is an integer from 0 to 5; and
$X_6$ is a halogen.

2. The compound of claim 1, wherein n is 2.
3. The compound of claim 1, wherein $X_6$ is I.
4. The compound of claim 1, having the formula:

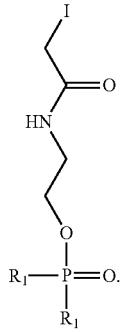

5. A pharmaceutical composition comprising the compound of claim 1 and a pharmaceutically acceptable carrier.

6. A method of inhibiting ribose 5-phosphate isomerase in a human, comprising administering to the human the pharmaceutical composition of claim 5.

7. A method of treating a mammal that is infected by a parasitic organism, the method comprising administering to the mammal the pharmaceutical composition of claim 5.

8. The compound of claim 1, wherein $X_1$ is P.
9. The compound of claim 1, wherein $X_1$ is S.
10. The compound of claim 9, having the formula:

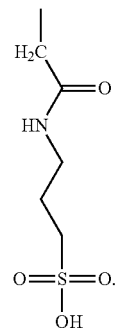

* * * * *

UNITED STATES PATENT AND TRADEMARK OFFICE
CERTIFICATE OF CORRECTION

Page 1 of 2

PATENT NO. : 10,336,777 B2
APPLICATION NO. : 15/888158
DATED : July 2, 2019
INVENTOR(S) : Edward L. D'Antonio It is certified that error appears in the above-identified patent and that said Letters Patent is hereby corrected as shown below:

In the Claims

In Column 8, Claim 1 reads/the chemical structure is:

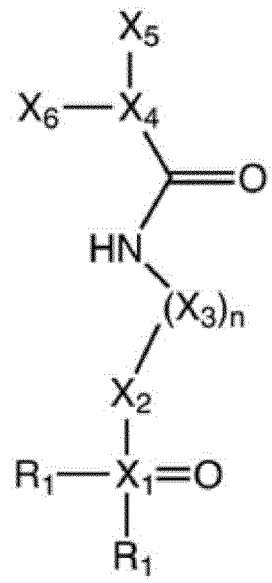

In Column 8, Claim 1 should read/the chemical structure should be:

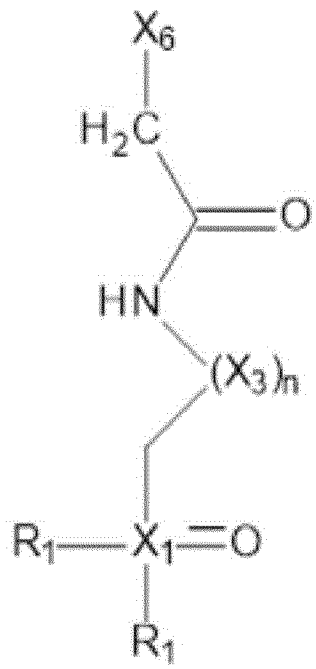

Signed and Sealed this
Fifth Day of November, 2019

Andrei Iancu
*Director of the United States Patent and Trademark Office*

CERTIFICATE OF CORRECTION (continued)
U.S. Pat. No. 10,336,777 B2

Page 2 of 2

In Column 8, Claim 4 reads/the chemical structure is:

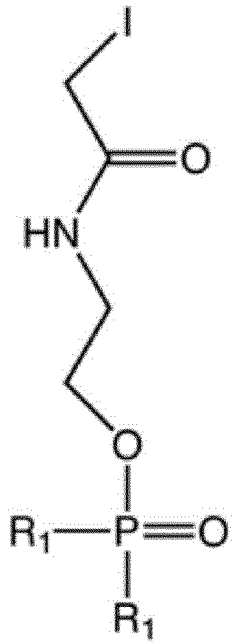

In Column 8, Claim 4 should read/the chemical structure should be:

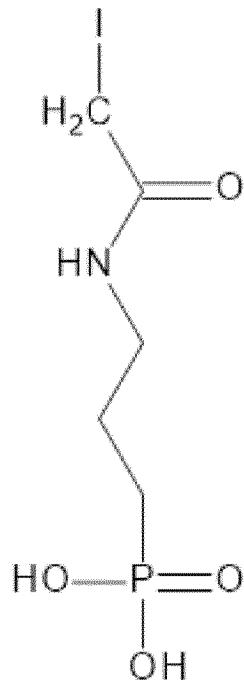

In Column 8, Claim 10 reads/the chemical structure is:

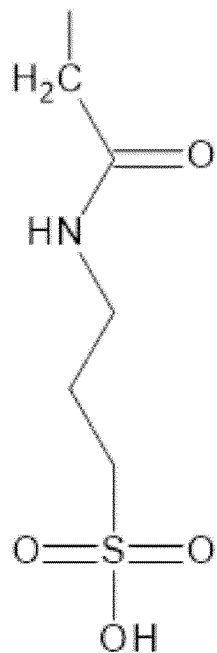

In Column 8, Claim 10 should read/the chemical structure should be: